United States Patent [19]

Smith et al.

[11] Patent Number: 5,143,450
[45] Date of Patent: Sep. 1, 1992

[54] APPARATUS FOR HANDLING DEVICES UNDER VARYING TEMPERATURES

[75] Inventors: Nathan R. Smith; Steven E. Schmitt, both of Stillwater, Minn.

[73] Assignee: Aetrium, Inc., North St. Paul, Minn.

[21] Appl. No.: 649,657

[22] Filed: Feb. 1, 1991

[51] Int. Cl.$^5$ .................... G01N 25/00; G01N 25/72
[52] U.S. Cl. .................................. 374/12; 374/57; 374/179; 269/903; 901/17
[58] Field of Search ................ 374/12, 45, 57, 208, 374/121, 120, 179; 269/21, 900, 903 X; 414/744.3, 744.6, 590, 750, 752; 901/17 X

[56] References Cited

U.S. PATENT DOCUMENTS

| | | |
|---|---|---|
| 2,842,942 | 7/1958 | Johnston et al. |
| 3,092,974 | 6/1963 | Haumann et al. |
| 3,176,499 | 4/1965 | Sikora . |
| 3,365,930 | 1/1968 | Arias . |
| 3,555,483 | 1/1971 | Tener . |
| 3,648,018 | 3/1972 | Cheng et al. |
| 3,691,840 | 9/1972 | Dufour et al. |
| 3,807,216 | 4/1974 | Lindwedel et al. |
| 3,817,084 | 6/1974 | Whitehead ............... 374/208 |
| 3,979,671 | 9/1976 | Meeker et al. |
| 4,102,150 | 7/1978 | Kountz . |
| 4,112,589 | 9/1978 | Palfrey et al. |
| 4,114,096 | 9/1978 | Chinery . |
| 4,172,993 | 10/1979 | Leach . |
| 4,286,391 | 9/1981 | Gerry . |
| 4,324,285 | 4/1982 | Henderson . |
| 4,397,101 | 8/1983 | Rickard . |
| 4,419,023 | 12/1983 | Hager, Jr. |
| 4,426,619 | 1/1984 | Demand . |
| 4,437,771 | 3/1984 | Cazzaniga . |
| 4,456,919 | 6/1984 | Tomita et al. |
| 4,483,629 | 11/1984 | Schwarz et al. ........... 374/57 X |
| 4,527,620 | 7/1985 | Pederson et al. ........ 269/903 X |
| 4,542,345 | 9/1985 | Tomasulo . |
| 4,575,257 | 3/1986 | Ogura et al. ............. 374/57 X |
| 4,603,228 | 7/1986 | Kamada . |
| 4,604,572 | 8/1986 | Horiuchi et al. |
| 4,626,167 | 12/1986 | Bond et al. ............... 414/752 X |
| 4,696,578 | 9/1987 | Mansuria et al. |
| 4,734,872 | 3/1988 | Eager et al. |
| 4,739,258 | 4/1988 | Schwarz . |
| 4,787,752 | 11/1988 | Fraser et al. |
| 4,793,716 | 12/1988 | Wei et al. |
| 4,831,845 | 5/1989 | Oda et al. |
| 4,856,766 | 9/1989 | Huberts ...................... 269/21 |
| 4,865,461 | 9/1989 | Taylor et al. |
| 4,871,965 | 10/1989 | Elbert et al. |
| 4,884,027 | 11/1989 | Holderfield et al. |
| 4,964,737 | 10/1990 | Baker et al. |

OTHER PUBLICATIONS

R. L. Bailey, *Technical Digest*, #44 Western Electric Company, 1076, pp.3–4.

*Primary Examiner*—William A. Cuchlinski, Jr.
*Assistant Examiner*—G. Bradley Bennett
*Attorney, Agent, or Firm*—Peterson, Wicks, Nemer & Kamrath

[57] ABSTRACT

Apparatus (10) for handling devices for testing under varying temperature conditions is disclosed including a mechanical arm (32) pivotally mounted by a bearing (34) to a control portion (16) which is variably vertically positionable relative to a platform portion (14). An insert arm (38) is rotatably mounted within the mechanical arm (32) to reciprocally and rotatably mount a thermal socket (90) for mating with a contactor (126). The socket (90) is mounted to a vacuum cup (48) to allow position alignment as alignment pins (132) are initially slideably received in alignment notches (124) and when no vacuum is applied and is fixed in the aligned position after the application of vacuum. Thermal tubes (74) of probes (50) are reciprocal with the thermal socket (90) to provide thermally conditioned gas/air to the thermal socket (90). The thermal socket (90) provides a swirling action to the thermally conditioned gas/air to exit 360° around a vacuum cup (112) holding the device in the thermal socket (90) for circulating the thermally conditioned gas/air across the top and past the leads of the device. The apparatus (10) monitors and controls the device core temperature by measuring the temperature of the bottom of the device and of a thermally spaced location of a pedestal (144) abutting the bottom of the device and determining the rate of heat flow through a temperature sensing loop.

13 Claims, 3 Drawing Sheets

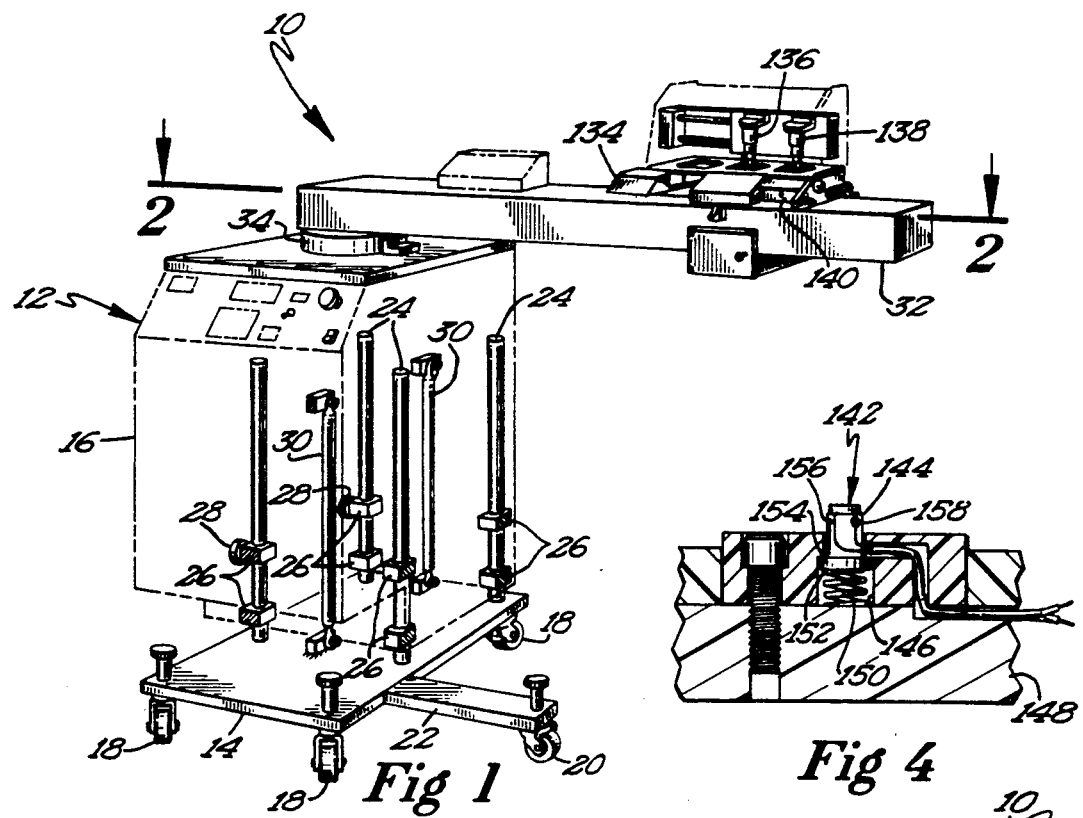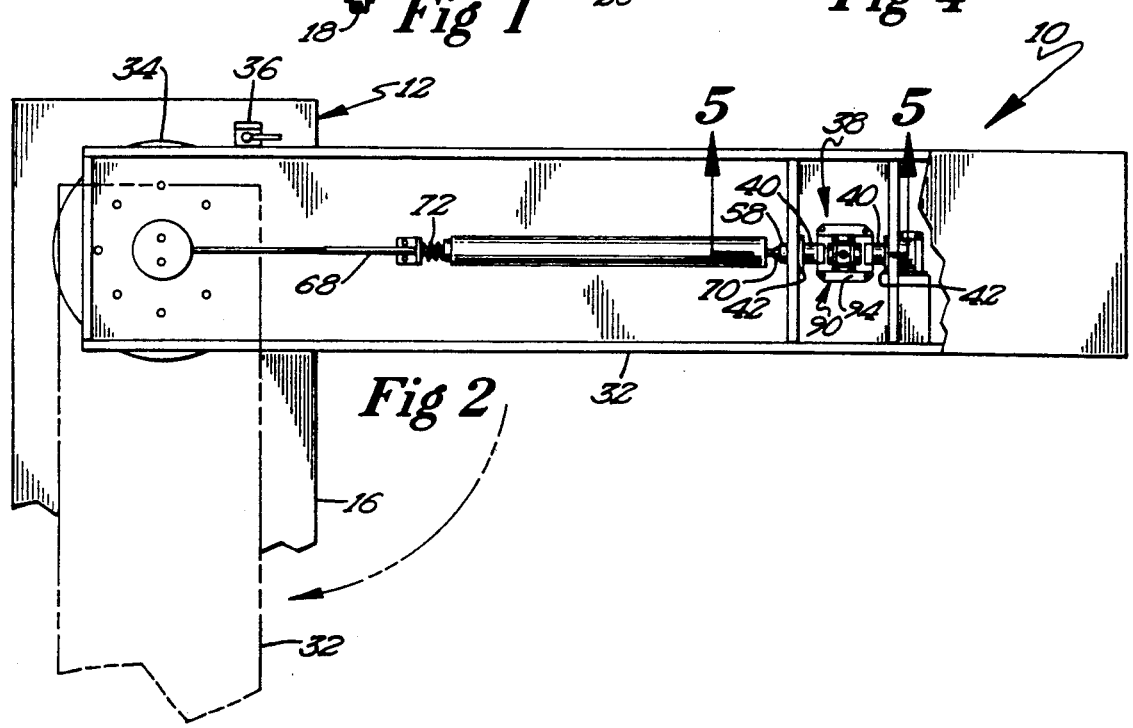

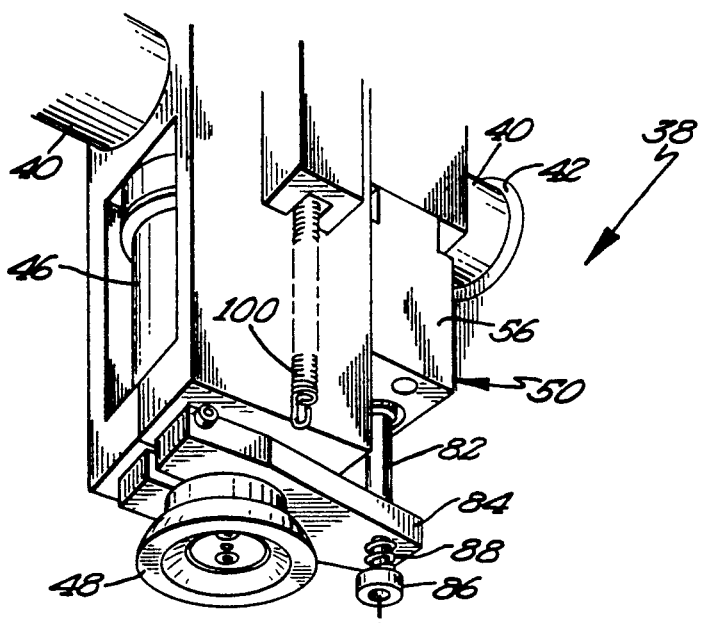
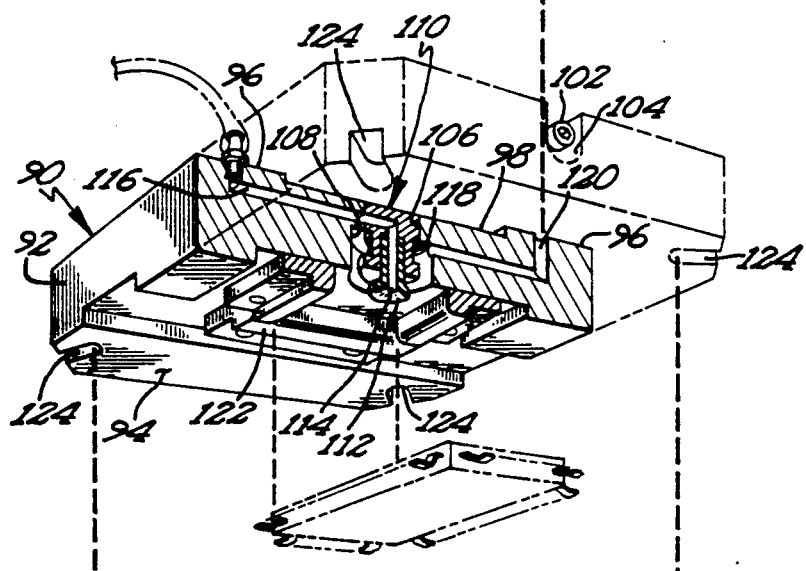
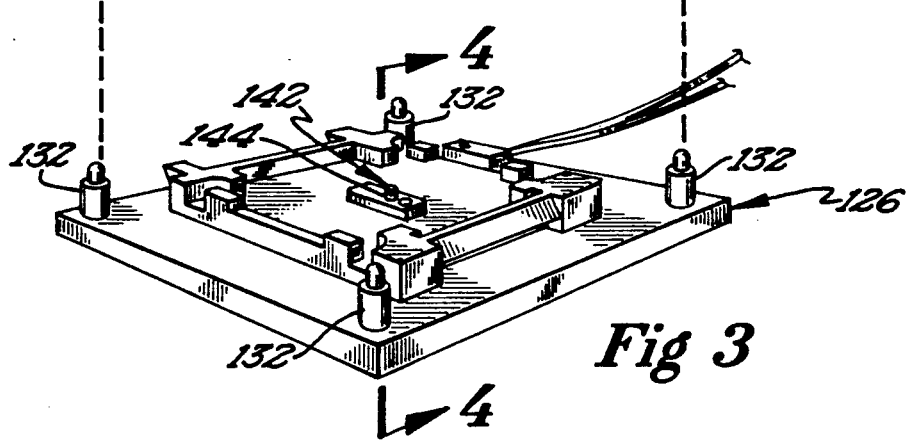
Fig 3
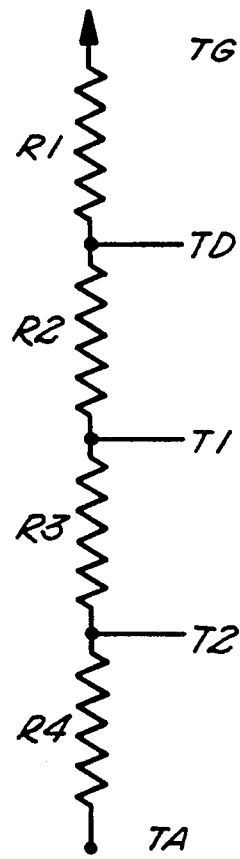
Fig 6

5,143,450

APPARATUS FOR HANDLING DEVICES UNDER VARYING TEMPERATURES

BACKGROUND

The present invention generally relates to devices for handling devices under test, such as integrated circuit packages, particularly to devices for handling such devices for testing under varying temperature conditions.

Integrated circuits are tested electrically and under specific thermal conditions to determine the reliability of such circuits. Such testing has been accomplished by a variety of ways. One prior method was thermal forcing systems which could be cumbersome, inconvenient, and tedious. Another previous method utilized was pick and place handlers which were inefficient and relatively expensive and thus were economically justifiable in only limited circumstances.

SUMMARY

It is thus an object of the present invention to provide a unique apparatus for handling devices such as integrated circuit packages for testing thereof. In a first aspect of the present invention, the apparatus is constructed to accommodate just about any size test head and to conform to a wide range of test head heights for easy docking and undocking. Further, the apparatus is of a compact size so it does not take up much space and also has easy mobility allowing it to pass through congested areas to the test location.

In a further object of the present invention, the apparatus provides fast changeover if testing of different devices having different package constructions is desired. In an aspect of the present invention, the conversion of the apparatus to handled different device package requires minimal part replacement and provides rapid self alignment.

In a further object of the present invention, the apparatus provides thermally conditioned gas to the thermal socket removably holding the device under test and which is rotatable and reciprocal. In an aspect of the present invention, a thermal tube is reciprocal and movable with the thermal socket and does not rely upon flexibility or bending material characteristics to allow fluid communication of thermally conditioned gas having a wide temperature range such as from −60° C. to 165° C.

In yet another object of the present invention, the apparatus directs the thermally conditioned gas in a manner to rapidly heat and cool the device under test to the set point temperature without exposing the device under test to extreme gas temperatures and without subjecting the test head to harsh temperatures.

In another object of the present invention, the apparatus monitors and controls the die or core temperature of the device under test to insure that thermal conditioning is both fast and accurate over the testing temperature range. In this regard, the exterior package temperature is measured and compared to the temperature at a known thermally spaced location to determine the core temperature based upon heat flow through a temperature sensing loop.

The present invention will become clearer in light of the following detailed description of an illustrative embodiment of this invention described in connection with the drawings.

DESCRIPTION OF THE DRAWINGS

FIG. 1 shows a perspective view of an apparatus for handling integrated circuit packages according to the preferred teachings of the present invention, with portions being shown in phantom to expose interior components.

FIG. 2 shows a partial, top view of the apparatus of FIG. 1, with portions being broken away to expose interior components and with portions being shown in phantom to show alternate positions.

FIG. 3 shows a partial, exploded view of the insert arm of the apparatus of FIG. 1, with portions being shown in phantom to expose constructional details.

FIG. 4 shows a partial, cross-sectional view of the apparatus of FIG. 1 according to section line 4—4 of FIG. 3.

FIG. 6 shows a diagrammatic view of the thermal model of the temperature monitoring and controlling system of the apparatus of FIG. 1.

Figure 5:
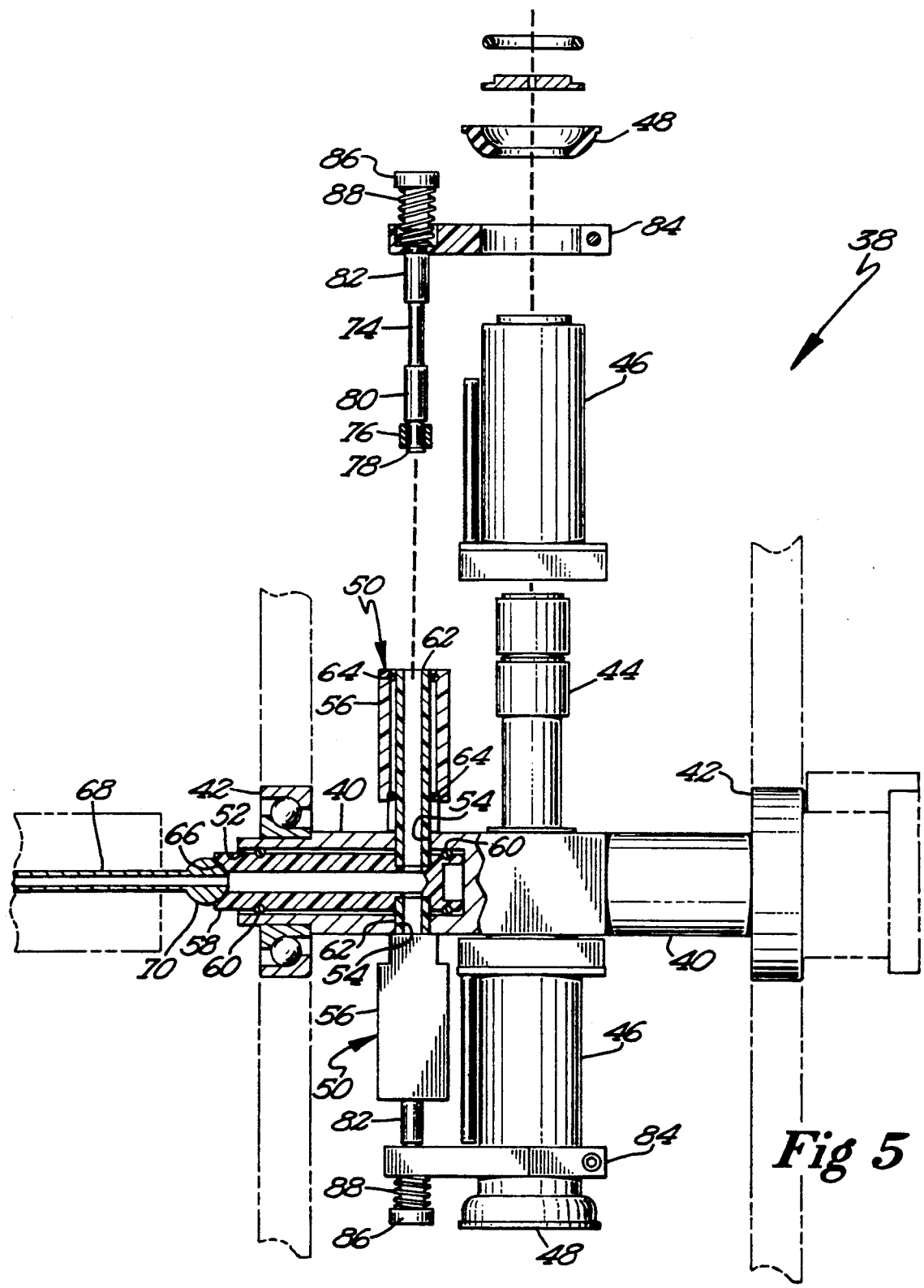
FIG. 5 shows a partial, cross-sectional view of the apparatus of FIG. 1 according to section line 5—5 of FIG. 2, with portions being exploded to expose constructional details.

All figures are drawn for ease of explanation of the basic teachings of the present invention only; the extensions of the Figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art after the following teachings of the present invention have been read and understood.

Where used in the various figures of the drawings, the same numerals designate the same or similar parts. Furthermore, when the terms "top", "first", "second", "vertical", "horizontal", "end", "side", and similar terms are used herein, it should be understood that these terms have reference only to the structure shown in the drawings as it would appear to a person viewing the drawings and are utilized only to facilitate describing the invention.

DESCRIPTION

Apparatus for handling devices such as integrated circuit packages, computer chips, or the like according to the preferred teachings of the present invention is shown in the drawings and generally designated 10. Generally, apparatus 10 includes a body 12 including a platform portion 14 and a control portion 16. In the most preferred form, body 12 is generally rectangular in horizontal cross section. Platform portion 14 includes four casters 18 located at the corners thereof and a fifth caster 20 located at the free end of a leg 22 extending generally perpendicularly from the side of platform portion 14. Casters 18 and 20 provide movable support of platform portion 14 and may include leveling provisions for facilitating a small degree of platform leveling if apparatus 10 is placed on an uneven surface. Platform portion 14 further includes four vertical, spaced guide shafts 24 located adjacent the corners of platform portion 14 and generally parallel to each other. Control portion 16 includes slide bearings 26 slideably received on shafts 24 for allowing control portion 16 to be raised or lowered relative to platform portion 14 by sliding bearings 26 on shafts 24 to variably vertically position control portion 16 relative to platform portion 14. Suitable provisions 28 are provided for locking bearings 26 at the desired position on shafts 24 and thus control portion 16 in the desired vertical position relative to platform portion 14. Means 30 such as gas springs as shown extending between portions 14 and 16 can be provided to balance the weight of control portion 16 and components associated therewith making it easier to raise or lower control portion 16 relative to platform portion 14.

Apparatus 10 further includes a mechanical arm 32 which is rotatably mounted by one end to the top of control portion 16 by a bearing 34. Arm 32 is rotatable 90° between a home position generally parallel to body 12 and generally perpendicular to leg 22 and an operative position extending from the same side of body 12 as leg 22 and generally parallel to and spaced from leg 22. Suitable provisions 36 can be provided for locking arm 32 in either its home or operative position.

An insert arm 38 is rotatably mounted within arm 32 adjacent to but slightly spaced from the free end of arm 32. Arm 38 generally includes a shaft 40 rotatably mounted about a horizontal axis generally parallel to the longitudinal axis of arm 32 by suitable bearings 42. First and second pistons 44 extend generally perpendicular to and on diametrically opposite sides of shaft 40. Cylinders 46 are reciprocally received on pistons 44 for relative travel thereto. Suitable provisions are provided for applying are pressure through pistons 44 and into cylinders 46 to extend cylinder 46 relative to piston 44 and for applying a vacuum through pistons 44 and into cylinders 46 to contract cylinder 46 relative to piston 44. A vacuum cup 48 is attached to the end of each cylinder 46, with suitable provisions also being provided for applying a vacuum to cups 48.

Arm 38 further includes first and second thermal probes 50. Specifically, shaft 40 includes an inner bore 52 extending parallel to the axis of shaft 40 and a cross bore 54 intersecting generally perpendicularly with bore 52 and generally in the same axial plane as pistons 44. First and second hollow sleeves 56 are secured generally perpendicular to shaft 40 generally contiguous to and in line with bore 54. A tube 58 having a cross-sectional size less than bore 52 is supported within bore 52 by first and second spaced O-rings 60. Secondary tubes 62 are supported in sleeves 56 and cross bore 54 by first and second spaced O-rings 64 and intersect with and are in fluid communication with tube 58. Secondary tubes 62 extend from tube 58 spaced from and parallel to pistons 44 and the direction of reciprocation of cylinders 46. Tubes 58 and 62 are formed of material which is resistant to thermal transfer such as Teflon ® or glass. Furthermore, the only physical contact between tubes 58 and 62 and shaft 40 and sleeves 56 are through O-rings 60 and 64, with tubes 58 and 62 being spaced from bores 52 and 54 and sleeve 56 to create a thermal air barrier to further reduce heat transfer between tubes 58 and 62 and shaft 40 and sleeves 56. It should be realized that the end of tube 58 within shaft 40 is closed. The inlet end of tube 58 extending out of bore 52 of shaft 40 includes a semi-spherical depression 66. The inlet tube 68 for the conditioned gas/air includes an enlarged spherically shaped end 70 for receipt within depression 66 to allow relative rotation and pivoting of tube 68 relative to shaft 40 and tube 58. Tube 68 is biased towards shaft 40 such as by spring 72 to insure that end 70 remains nested inside of depression 66 even with thermal expansion or contraction of tube 68. Tube 68 can be in fluid communication with a source of gas/air which may be conditioned to the desired temperature. For example, tube 68 may be in communication with a source of nitrogen gas for providing cold temperatures and with a source of air which may be electrically or otherwise heated for providing hot temperatures.

First and second thermal tubes 74 having cross sectional sizes less than that of the passages through tubes 62 are provided for reciprocal receipt inside of tubes 62. An annular piston 76 is provided including an outer surface of a size generally equal to and for reciprocal receipt within and in sealing engagement with the passage of tube 62 and including an inner surface of a size greater than and for reciprocally receiving thermal tube 74. Piston 76 is slideable on thermal tube 74 but is captured on thermal tube 74 by a flange 78 integrally formed on the inside end of tube 74 and a silicon rubber or other elastic piston retainer 80 located on tube 74. Tube 74 further includes a silicon rubber or other elastic stroke limiting device 82 similarly positioned on tube 74 but spaced from piston retainer 80. Due to their elastic nature, piston retainer 80 and device 82 can be forced to slide on tube 74 but will remain at that position when the assembly force is removed. Tube 74 extends through and reciprocally passes through an aperture formed in an attachment bracket 84, with the opposite end of tube 74 terminating in a collar 86. Collar 86 is formed of suitable material such as Teflon ® for reducing heat transfer. Tube 74 is biased relative to bracket 84 by a spring 88 sandwiched between collar 86 and bracket 84, with device 82 limiting the movement of tube 74 relative to bracket 84. Bracket 84 is secured to cylinders 46 for reciprocal movement therewith. Retainer 80 and device 82 have an outer diameter less than the passages of tubes 62 and tube 74 has considerable tolerance to tip within piston 76 and the aperture formed in bracket 84 such that in addition to reciprocal movement, tube 74 and collar 86 mounted thereto are allowed to tip and move relative to piston 76 and tube 62.

Arm 38 in the most preferred form includes a thermal socket 90. Socket 90 generally includes a base 92 having a first surface 94 and a second surface 96. Surface 96 includes a depression 98 of a size and shape complementary to but larger than vacuum cups 48. When vacuum is applied to vacuum cups 48, vacuum cups 48 will adhere to surface 96 inside of depression 98 and thus secure thermal socket 90 to cylinders 46 for reciprocation therewith. For retaining thermal socket 90 upon vacuum cup 48 when a vacuum is not applied to vacuum cups 48, first and second springs 100 are provided having their first ends anchored to shaft 40 by any suitable means and having their second ends removably attached to pins 102 secured in base 92 of thermal socket 90. In the most preferred form, pins 102 are located in recesses 104 formed in base 92 extending from surface 96 and intersecting with a side of base 92. It can be appreciated that although springs 100 are tensioned to firmly hold thermal socket 90 against vacuum cup 48 in the direction of reciprocation and expand and contract with the reciprocation of thermal socket 90, thermal socket 90 is able to slide side-to-side on vacuum cup 48 generally perpendicular to the direction of reciprocation when no vacuum is applied thereto, with the extent of movement being restricted by abutment of vacuum cup 48 with the sides of depression 98.

Base 92 further includes a first bore 106 extending perpendicularly from surface 96 and intersecting concentrically within a second bore 108 extending perpendicularly from surface 94, with the cross sectional size of bore 108 being greater than that of bore 106. An insert 110 is provided having an outside surface of a size and shape complementary to and for press fitting into bore 106. A vacuum cup 112 for removable attachment to the device under test is located on the end of insert 110 and is received in the internal bore 114 of insert 110. An internal passage 116 is provided in vacuum cup 112, insert 110, and base 92 for connection to a source of air pressure and/or vacuum. Insert 110 further includes an annular groove 118 located above bore 106, inside of bore 108, and below surface 94, vacuum cup 112 and the free end of insert 110. A passageway 120 is provided in base 92 having an inlet in fluid communication with collar 86 of thermal tube 74 abutting with base 92 and an outlet in fluid communication with bore 108 and in the same plane as groove 118 of insert 110. Suitable provisions 122 are provided on surface 94 for mechanically supporting the electrical leads of the device under test when such device is secured to vacuum cup 112. Alignment notches 124 are formed in base 92 extending from surface 94 and intersecting with a side of 92.

Thermal socket 90 is reciprocal relative to and mates with a contactor 126 of a test head for testing the device under test. Specifically, contactor 126 includes electrical contacts for electrically contacting the electrical leads of the device under test. Further, contactor 126 mates with thermal socket 90 to generally thermally isolate the device under test secured to vacuum cup 112 of thermal socket 90. Additionally, contactor 126 includes alignment pins 132 complementary to and for slideable receipt within alignment notches 124 of thermal socket 90. With pins 132 received in notches 124, socket 90 is aligned with contactor 126 such that the electrical contacts contact the leads of the device under test without damage to the device and/or its leads and such that the device is thermally isolated within thermal socket 90 and contactor 126.

It can then be appreciated that apparatus 10 according to the preferred teachings of the present invention allows ease of changeover of thermal socket 90 and contactor 126 when different types of devices are to be tested. Specifically, contactor 126 is positioned on the test head in the normal manner. Thermal socket 90 may then be placed upon vacuum cup 48 and held thereon by springs 100 attached to pins 102. As cylinder 46 is extended to mate thermal socket 90 with contactor 126, alignment pins 132 extend into notches 124. As thermal socket 90 is allowed to move side to side on vacuum cup 48 and collar 86 without vacuum applied to vacuum cup 48, notches 124 and base 92 will move to align with pins 132 and contactor 126 to thereby align socket 90 with contactor 126. After socket 90 has been mated or nested on contactor 126, vacuum is then applied to vacuum cup 48 to secure socket 90 to vacuum cup 48 in the aligned position. Vacuum can then be continuously supplied to vacuum cup 48 during operation of apparatus 10 until it becomes necessary to change socket 90 and contactor 126 when another type of device is desired to be tested or the like. Although technically springs 100 can be removed from pins 102 after vacuum has been supplied to vacuum cup 48, springs 100 can be left connected to socket 90 for convenience of storage.

It should be noted that in addition to the two axis alignment provided by pins 132 received in notches 124, vacuum cup 48 allows socket 90 and contactor 126 to be parallel to each other. Specifically, due to the inherent flexible nature of vacuum cup 48, vacuum cup 48 provides all six degrees of freedom of movement to thermal socket 90 secured thereto, i.e. along X and Y axes, to pivot in either direction along the X axis, and/or to pivot in either direction along the Y axis. Prior to the present invention, the member for holding the device in the testing head was solidly mounted to the reciprocating cylinders. Thus, complicated adjustment was required to position the holding member on the reciprocating cylinders to exactly match the testing head, with such adjustment being very mechanically complicated and time consuming. Apparatus 10 allows the automatic adjustment of thermal socket 90 relative to contactor 126 by simply turning off and on the source of vacuum to vacuum cup 48.

It should further be noted that probes 50 according to the preferred teachings of the present invention are also advantageous in use with the securement of thermal socket 90 by vacuum cup 48 when it is desired to provide thermally conditioned air/gas to thermal socket 90. Specifically, spring 88 biases collar 86 of thermal tube 74 to abut thermal socket 90 at all times. Further, any variance in the radial spacing between thermal socket 90 and shaft 40 is compensated by the extent that thermal tube 74 is located within secondary tubes 62. Furthermore, any variance in the angular positioning of thermal socket 90 and cylinder 46 is compensated by thermal tube 74 pivoting inside piston 76 and bracket 84 to match that of thermal socket 90 and by collar 86 sliding on surface 96 of thermal socket 90. It can then be appreciated that collar 86 abuts flushly with thermal socket 90 in all positions to insure that uninterrupted fluid communication is provided between probes 50 and passageway 120 of thermal socket 90 without leaking and without thermal tubes 74 interfering with the freedom of movement of thermal socket 90 provided by the novel attachment method of the present invention utilizing vacuum cups 48.

It should also be noted that probes 50 according to the preferred teachings of the present invention are also advantageous in use in providing communication of a thermally conditioned gas/air to thermal socket 90 which is rotating about the axis of shaft 40 and is also reciprocal radially with respect to the axis of shaft 40. Specifically, the material utilized in flexible tubing which can allow relative movement between parts under certain temperature ranges typically does not allow such relative movement in extreme temperature environments such as that for the testing of integrated circuits, i.e. in the range of $-60°$ C. to $165°$ C. The most common way of avoiding this problem in prior testing apparatus was to enclose the entire testing system. However, this has severe shortcomings as considerable energy (and time) was required to heat or cool the enclosure as well as the mass of the testing system itself in addition to the device under test, and also subjecting the testing system to undesirable temperature extremes. Apparatus 10 avoids this problem by the use of probes 50 according to the teachings of the present invention utilizing thermal tubes 74 which reciprocate (and move) with thermal socket 90. Specifically, probes 50 can be formed of material which is able to withstand the temperature extremes and of components which do not rely on their material flexibility to provide relative movement therebetween. Thus, it is not necessary to thermally condition the entire testing system as was done previously, but rather thermal conditioning can be isolated, greatly reducing the energy and time required to subject the device to the desired testing temperatures.

It should be appreciated that thermal socket 90 according to the teachings of the present invention is advantageous in thermal conditioning the device to be tested. Specifically, thermal socket 90 generally limits the thermally conditioned gas/air to the device under test and its immediate surroundings. In addition to greatly reducing energy use and time, exposure of the sensitive test head to the harsh temperatures of the thermally conditioned gas is virtually eliminated.

Further, with the top of the device under test being secured to vacuum cup 112, the thermally conditioned gas/air is circulated only across the top of the device and past the leads of the device in the preferred form of thermal socket 90 according to the preferred teachings of the present invention. Due to the superior heat transfer characteristics of this circulation process, the temperature of the device under test rises quickly in a linear approach to the set point temperature.

It is further believed that the manner of distribution of the thermally conditioned gas/air within thermal socket 90 and contactor 126 and around the device under test is advantageous. Specifically, in the preferred form, the cross sectional size of bore 108 is larger than that of vacuum cup 112 creating an annular passage out of base 92 defined by bore 108 and by insert 110 and vacuum cup 112. The thermally conditioned gas/air flowing from passageway 120 flows into groove 118 formed in insert 110 and located within bore 108 provides a swirling action as it engages insert 110 within groove 118 to flow around insert 110 and exit 360° around vacuum cup 112 through the annular passage defined by bore 108, insert 110 and vacuum cup 112. Thus, relatively even distribution of the thermally conditioned gas/air occurs around the device under test.

Now that the basic construction of apparatus 10 according to the preferred teachings of the present invention has been explained, the operation and a preferred application of apparatus 10 can be set forth. Specifically, with mechanical arm 32 in its home position, apparatus 10 can be wheeled on casters 18 and 20 to the test location. It can then be appreciated that with arm 32 in its home position, the width of apparatus 10 is such to allow its movement through doorways and the like congested areas to the test location.

With control portion 16 positioned relative to platform portion 14 such that mechanical arm 32 is located above the test head, locking provisions 36 are released allowing mechanical arm 32 to be pivoted on bearing 34 to its operative position and then locked therein utilizing locking provisions 36. After release of locking provisions 28, control portion 16 is lowered relative to platform portion 14 by sliding bearings 26 on guide shafts 24 against the bias of gas springs 30 until mechanical arm 32 engages and docks with the test head, with control portion 16 being locked in position utilizing provisions 28. It can also be appreciated that casters 18 and 20 may be adjusted to compensate for any unevenness in the floor to insure that mechanical arm 32 is generally parallel to the floor. Caster 20 positioned on the free end of leg 22 counteracts any tipping force created due to the cantilever type positioning of mechanical arm 32 on control portion 16 and to the placement of downward forces adjacent the free end of mechanical arm 32. It should be noted that to undock mechanical arm 32 from the test head, the docking procedure is simply reversed. It can also be appreciated that apparatus 10 according to the teachings of the present invention includes self-contained docking and undocking features allowing fast changeover if testing is desired to be converted from one device package to another or allowing ease of placement, removal and transport of apparatus 10 relative to the test head.

In a preferred form, an operator using a vacuum wand places a device to be tested in a placement nest mounted inside of an input drawer 134. Drawer 134 closes placing the device to be tested under a probe 136. Probe 136 extends to pick the device to be tested from the placement nest of input drawer 134, retracts, and moves to a position corresponding to thermal socket 90. With cylinder 46 and thermal socket 90 in its extended condition, probe 136 places the device to be tested within thermal socket 90 and vacuum is applied to vacuum cup 112 to secure the device to be tested within thermal socket 90. Probe 136 then releases the device to be tested, retracts, and moves back to its original position for picking up the next device to be tested. Thereafter, cylinder 46 and thermal socket 90 retract and insert arm 38 rotates 180° about shaft 40 to thus place the device to be tested above contactor 126. Cylinder 46 and thermal socket 90 extend to mate thermal socket 90 with contactor 126. It should be recognized that it has been assumed that thermal socket 90 has been previously aligned upon vacuum cup 48 to insure that thermal socket 90 is aligned with contactor 126. It should be noted that thermal socket 90 mounted on cylinder 46 on the opposite side of shaft 40 is then in a position for removing the device which had just previously been tested as will be explained hereinafter and for receiving the next device to be tested.

After mating of thermal socket 90 with contactor 126, thermally conditioned gas/air can be introduced through probe 50 to thermal socket 90 to place the device to be tested under the temperature(s) at which the tests are desired. After testing has been completed, thermal socket 90 and cylinder 46 is retracted, separating thermal socket 90 from contactor 126. Insert arm 38 rotates in the opposite direction 180° about shaft 40 to thus place the device to be tested in an upper position. It should again be noted that thermal socket 90 mounted on cylinder 46 on the opposite side of shaft 40 is then in a position above contactor 126 preparing the next device for testing.

After rotation of insert arm 38, cylinder 46 and thermal socket 90 are extended and a second probe 138 positioned thereabove extends and attached to the device tested. After attachment, vacuum to vacuum cup 112 is released and probe 138 retracts. It can then be appreciated that thermal socket 90 is then ready to accept the next device to be tested. Probe 138 moves to a position corresponding to the placement nest of an output drawer 140. It should be noted that probes 136 and 138 can be interconnected to simultaneously move to their respective positions. Probe 138 is then extended to place the device within the placement nest of output drawer 140. After release of the device, probe 138 is retracted and output drawer 140 opens giving access to the device for removal from the placement nest of output drawer 140 by the operator using the vacuum wand.

It should then be appreciated that insert arm 38 of apparatus 10 of the preferred teachings of the present invention is advantageous for several reasons. First, insert arm 38 provides automatic insertion of the device under test into contactor 126 eliminating manual errors, minimizing lead damage, and improving productivity. Particularly, thermal socket 90 insures that the device under test is secured in position with provisions 122 supporting the device leads both during placement with contactor 126 as well as during the thermal conditioning and testing cycles. The adjustment feature of thermal socket 90 with cylinder and with contactor 126 together with the freedom of movement provided by the flexibility of vacuum cup 48 and the non-interfering relationship of probes 50 with the movement of thermal socket 90 assures accurate placement of the device under test and lead protection. Further, the force at which thermal socket 90 and the device under test secured thereto engages contactor 126 can be easily controlled by the application of air pressure through pistons 44 to cylinders 46. It can then be appreciated that automatic package insertion, precision alignment, and high performance contacting is accomplished in one quick, efficient motion, i.e. the extension of cylinder 46 on piston 44.

It can also be appreciated that apparatus 10 according to the preferred teachings of the present invention is particularly advantageous for small to medium volume environmental testing applications because it is easier and faster to use than prior thermal forcing systems, yet costs significantly less than prior pick and place handlers.

Apparatus 10 according to the preferred teachings of the present invention includes provisions 142 to monitor and control the die or core temperature of the device to be tested. In the most preferred form, contactor 126 includes a plastic pedestal 144 of contactor 126. Pedestal 144 is biased outwardly in bore 146 towards the bottom of the device under test within the mating thermal socket 90 and contactor 126 such as by a spring 150. Pedestal 144 may be retained in bore 146 by suitable means such as an enlarged lip 152 which engages with a shoulder 154 formed in bore 146. A copper disc 154 is secured to the outside face of pedestal 144. A first, type T thermocouple 156 is secured such as by soldering to disc 154 and sandwiched between pedestal 144 and disc 154 for measuring the temperature of the bottom of the device under test. A second, type T thermocouple 158 is secured to pedestal 144 such as by plastic bonding for measuring the temperature of pedestal 144 at a location thermally spaced from thermocouple 156 by a thermal resistance. Thermocouple 156 and 158 generate an electrical signal as a function of the temperature at their respective locations.

When an electrical test is performed on an integrated circuit device at a non-ambient temperature, the device die temperature is to be within a desired guard band tolerance of the designated set-point test temperature. In prior environmental chambers, the entire chamber is regulated at the set-point temperature. When a device first enters the chamber, the change in the temperature of the device per unit change in time is large. As the device is warmed or cooled and its temperature nears the set-point temperature, the rate of temperature change is less rapid. This characteristic explains the asymptotic nature of the rate at which a thermal mass placed in a temperature chamber is heated or cooled. To raise device temperature close to the set-point in a chamber is not a problem, it is the last few degrees where the time is increased. When the device case temperature matches set-point temperature, after some preset soak exposure time has elapsed, it is assumed that case temperature and die temperature are both at set-point temperature. However, this is true only if there is not heat flow through the device. In order to assure that this condition exists, the soak exposure time period is typically longer than necessary.

In contrast to the environmental chamber process which monitors the environment, apparatus 10 according to the preferred teachings of the present invention monitors and controls the temperature of the device to be tested. Apparatus 10 utilizes the differences in the temperatures as measured by thermocouples 156 and 158 and the determinable thermal resistance between thermocouples 156 and 158 and between the package die of the device to be tested and thermocouple 156. Particularly, heat flows through an object similar to current flow in a circuit. Ohms Law formula for electricity is $E=IR$ and the formula for heat flow through an object is $T=qR$ where T is Temperature, q is heat flow, and R is thermal resistance. This formula simply states the temperature drop across some body is equal to the heat flow times the thermal resistance. Therefore, in comparing both formulas, heat flow is an analog to current; voltage drop is an analog to temperature; and thermal resistance is an analog to electrical resistance.

The thermal model of an integrated circuit device in thermal socket 90 of apparatus 10 according to the preferred teachings of the present invention is depicted in FIG. 6 where R1 is thermal resistance between the thermal conditioned gas/air and the package die; R2 is thermal resistance between the package die and thermocouple 156; R3 is thermal resistance between thermocouples 156 and 158; R4 is thermal resistance between thermocouple 158 and ambient temperature; TG is the temperature of the thermally conditioned gas/air; TD is the temperature of the package die; T1 is the temperature at thermocouple 156; T2 is the temperature at thermocouple 158; and TA is the ambient temperature. Thus, for example, when heating a device under test above ambient, if the thermally conditioned gas/air temperature TG is 100° C., the die temperature TD may be at some lower temperature, say 90° C.; the temperature near the electrical leads of the device under test may be 85° C., and temperature T1 measured by thermocouple 156 located on the bottom of the device under test, may be 80° C. The temperature differences are due to heat flow through the device under test as its temperature is being raised to the set-point temperature.

Thus, the die temperature TD can be sensed indirectly by thermocouples 156 and 158. Thermal resistance R3 between thermocouples 156 and 158 is a known value. With heat flowing through the device under test, there is an effective thermal resistance from the die of the device to thermocouple 156. The bottom of the device under test is pressed against thermocouple 156 in contactor 126 creating a repeatable environment. Thus, experimentally, resistance value R2 between the package die and thermocouple 156 can be determined. Heat flow q is calculated by determining the temperature difference between thermocouples 156 and 158 divided by the thermal resistance R3 between thermocouples 156 and 158 ($q=(T1-T2)/R3$). Since the thermal resistance R2 has been determined, die temperature TD can therefore also be determined. Specifically, die temperature TD is equal to temperature T1 of thermocouple 156 plus the heat flow q multiplied by thermal resistance R2 ($TD=T1+q\times R2$).

The temperature difference between thermocouples 156 and 158, together with the values of the various thermal resistances R illustrated in the thermal model of FIG. 6, establishes the dynamic heat flow characteristics of the device under test and enables software to determine actual die temperature TD. Given this information, apparatus 10 according to the preferred teachings of the present invention is able to accurately monitor and control temperature TD at the desired set-point temperature.

Specifically, thermally conditioned gas/air is circulated past vacuum cup 112, across the top of the device under test, and past the leads of the device under test. With the device positioned in contactor 126, the bottom of the device case contacts copper discs 154 and the temperature sensing loop is closed on the device under test. If the device under test in contactor 126 is not at set-point temperature, the temperature and/or flow rate of the gas are automatically adjusted by the thermal conditioning control system to bring the device under test to the set-point temperature. Once the device under test in contactor 126 is near the set point temperature, the gas temperature and/or flow rate is automatically reduced thereby achieving a rapid linear approach to the set point temperature without exposing the devices under test to extreme gas temperatures.

In the most preferred form, the next device to be tested located in thermal socket 90 on the opposite end of insert arm 38 than contactor 126 receives a similar amount of conditioning from the thermally conditioned gas/air as the device under test located in contactor 126 and the mating thermal socket 90. Thus, apparatus 10 according to the preferred teachings of the present invention conditions two devices to be tested at the same time, one in the lower thermal socket 90 mating with contactor 126 and the other in the upper thermal socket 90. Thus, thermal conditioning beings immediately after the device is placed into the available thermal socket 90 preparing the device for test so that it can be more rapidly brought to set point temperature during the next testing cycle.

In order to obtain an accurate reference for the sensing and control system of apparatus 10 according to the preferred teachings of the present invention, calibration and compensation parameter values for a particular combination of device, contactor 126, and thermal socket 90 are required. In many instances, a "golden device" can be used to obtain this data. The availability of such a golden device is relatively convenient as the majority of semiconductors include blocking diode junctions from the input of the device to the substrate which permit a specific amount of current to be conducted. These diodes have repeatable current flow voltage drop characteristics at specific temperatures. These diodes react like a thermometer. If an accurate voltmeter is connected across this junction, it is possible to measure the voltage across the diode.

The relationship between device die temperature TD and the current and voltage values of a diode junction for a device which is to be used as a golden device for temperature calibration purposes can be determined by measuring the values of the voltage and current for a diode junction with the golden device stabilized at various known temperatures. Once this relationship is determined, the golden device can be placed into thermal socket 90 of apparatus 10 according to the preferred teachings of the present invention, inserted into contactor 126, and thermal conditioned to the required set-point temperature(s). The voltage and current values for the blocking diode can be monitored through the contactor lead wires. The golden device, acting as a thermometer, provides temperature data required to establish the values for the calibration parameters of temperature sensing and control system of apparatus 10.

Now that the basic teachings of the present invention have been explained, many extensions and variations will be obvious to one having ordinary skill in the art. For example, in the preferred form, apparatus 10 according to the teachings of the present invention incorporates several unique features offering needed capabilities for engineering characterization, production lot sampling, and incoming inspection applications and it is believed that such incorporation produces synergistic results. However, it can be appreciated that such features can be utilized separately or in a variety of other combinations according to the teachings of the present invention.

Likewise, although shown and described utilizing manual placement and removal of the device under test into apparatus 10, it can be appreciated that automated placement and removal features can be utilized with apparatus 10 according to the teachings of the present invention.

Further, although the preferred mode of the present invention as shown and described resides in the environmental testing and handling of integrated circuit devices, the teachings of the present invention may have applications in other fields.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. Apparatus for handling and thermally conditioning devices utilizing thermally conditioned gas, with the device having a bottom and a core, comprising, in combination: a shaft having an inner bore; means for rotatably mounting the shaft about an axis; a thermal socket; means for removably attaching the device to the thermal socket; a contactor for mating with the thermal socket with the device located within the mating thermal socket and the contactor; means for reciprocating the thermal socket relative to the shaft in a first direction for mating with the contactor, with the reciprocating means including means for removably connecting to the thermal socket with a vacuum; means for holding the thermal socket against the removably connecting means in the first direction at least when vacuum is not being applied to the removably connecting means, with the thermal socket being movable relative to the connecting means generally perpendicular to the first direction when vacuum is not being applied to the removably connecting means; alignment pins secured to one of the thermal socket and the contactor; alignment notches formed in the other of the thermal socket and the contactor, with the alignment pins being slideably received within the alignment notches to align the mating of the thermal socket and the contactor, with the alignment pins and notches moving the thermal socket on the removably connecting means into alignment with the contactor when vacuum is not being applied to the removably connecting means and as the thermal socket and the contactor are being mated and with the application of vacuum to the connecting means connecting the thermal socket to the contactor; a first tube located in the inner bore of the shaft and rotatable about the axis, with the first tube including an inlet for the thermally conditioned gas; a secondary tube intersecting and in fluid communication with the first tube, with the secondary tube extending from the first tube spaced from and parallel to the first direction of the reciprocation of the thermal socket; a thermal tube having a first end reciprocally received within and in sealing engagement with the secondary tube and having a second end in fluid communication with the thermal socket, with the thermal tube reciprocating within the secondary tube with the reciprocation of the thermal socket; with the thermal socket comprising, in combination: a base; a first bore formed in the base having a size; an insert having an end and an outside surface of a shape complementary to but of a size smaller than the size of the bore, with the outside surface of the insert being concentrically located within the bore to form an annular gap between the bore and the insert, with the device removably attaching means located on the end of the insert; and a passageway formed in the base and in fluid communication with the second end of the thermal tube, with the passageway terminating in the bore with the thermally conditioned gas flowing into the annular gap.

2. The apparatus of claim 1 further comprising, in combination: a pedestal having an end and a thermal resistance, with the end of the pedestal engaging with the bottom of the device when the thermal socket is mated with the contactor; first means for determining the temperature of the bottom of the device; and second means for determining the temperature of the pedestal at a location thermally spaced from the first determining means by a thermal resistance.

3. The apparatus of claim 1 further comprising, in combination: a platform portion; a control portion having a top; means for variably vertically positioning the control portion relative to the platform portion; a mechanical arm; and means for pivotably mounting the mechanical arm to the top of the control portion between a home position generally parallel to the control portion and an operative position generally perpendicular to the control portion, with the shaft being rotatably mounted in the mechanical arm.

4. Thermal socket for removable connection to a device comprising, in combination: a base; a first bore formed in the base having a size; an insert having an end and an outside surface of a shape complementary to but of a size smaller than the size of the bore, with the outside surface of the insert being concentrically located within the bore to form an annular gap between the bore and the insert; means on the end of the insert for removably connecting to the device; an annular groove formed on the outside surface of the insert below the end and within the bore; and a passageway formed in the base and in fluid communication with a source of thermally conditioned gas, with the passageway terminating in the bore with the thermally conditioned gas flowing into the annular groove providing a swirling action to the thermally conditioned gas engaging the insert.

5. The thermal socket of claim 4 wherein the removably connecting means comprises a vacuum cup in fluid communication with a source of vacuum.

6. The thermal socket of claim 4 further comprising, in combination: a second bore intersecting with the first bore, with the second bore being of a shape and size complementary to and for press receipt of the insert.

7. Apparatus for providing a thermally conditioned gas to an object, with the object being rotatable about an axis and with the object being reciprocal in an angular direction with respect to the axis, comprising, in combination: a first tube rotatable about the axis, with the first tube including an inlet for the thermally conditioned gas; a secondary tube intersecting and in fluid communication with the first tube, with the secondary tube extending at an angle from the first tube spaced from and parallel to the angular direction of the reciprocation of the object; a thermal tube having a first end reciprocally received within and in sealing engagement with the secondary tube and having a second end in fluid communication with the object; and means for reciprocating the thermal tube within the secondary tube with the reciprocation of the object.

8. The apparatus of claim 7 wherein the object is reciprocated by means for reciprocating the object; and wherein the means for reciprocating the thermal tube comprises means for connecting the thermal tube to the means for reciprocating the object.

9. The apparatus of claim 8 wherein the connecting means comprises, in combination a bracket secured to the means for reciprocating the object, with the bracket reciprocally receiving the thermal tube; and means for biasing the thermal tube relative to the bracket.

10. The apparatus of claim 9 wherein the second end of the thermal tube includes a collar for abutting with the object; and wherein the biasing means comprises a spring sandwiched between the bracket and the collar.

11. The apparatus of claim 10 wherein the collar is slideable relative to the object; and wherein the thermal tube is pivotable within the secondary tube, with the thermal tube including an annular piston having an outer surface and an inner surface, with the outer surface being of a size for reciprocal receipt within and in sealing engagement with the secondary tube, with the inner surface of a size greater than that of the thermal tube for reciprocally receiving the thermal tube, and with the bracket including an aperture of a size greater than that of the thermal tube for reciprocally receiving the thermal tube.

12. The apparatus of claim 7 wherein the axis is defined by a shaft having an inner bore, with the inner bore having a size greater than that of the first tube, and wherein the apparatus further comprises, in combination: means for supporting the first tube within the inner bore creating a thermal air barrier to reduce heat transfer between the first tube and the inner bore.

13. The apparatus of claim 7 wherein the inlet of the first tube includes a semi-spherical depression; and wherein the apparatus further comprises, in combination: an inlet tube having an enlarged spherically shaped end for receipt in the depression; and means for biasing the spherically shaped end into the depression.

* * * * *